US010710129B2

(12) United States Patent
Vandenbruwane (10) Patent No.: US 10,710,129 B2
(45) Date of Patent: Jul. 14, 2020

(54) METHOD AND DEVICE FOR TREATING SOIL

(71) Applicant: INJECTIS BVBA, Waregem (BE)

(72) Inventor: Jeroen Vandenbruwane, Waregem (BE)

(73) Assignee: INJECTIS BVBA (BE)

(*) Notice: Subject to any disclaimer, the term of this patent is extended or adjusted under 35 U.S.C. 154(b) by 0 days.

(21) Appl. No.: 16/101,245

(22) Filed: Aug. 10, 2018

(65) Prior Publication Data

US 2019/0291153 A1 Sep. 26, 2019

(30) Foreign Application Priority Data

Mar. 23, 2018 (BE) .................................. 2018/5199

(51) Int. Cl.
| | |
|---|---|
| *B09C 1/08* | (2006.01) |
| *B09C 1/00* | (2006.01) |
| *G01N 33/24* | (2006.01) |
| *E02D 5/66* | (2006.01) |
| *E02D 7/22* | (2006.01) |
| *E02D 3/12* | (2006.01) |

(52) U.S. Cl.
CPC ................ *B09C 1/08* (2013.01); *B09C 1/002* (2013.01); *E02D 3/12* (2013.01); *E02D 5/66* (2013.01); *E02D 7/22* (2013.01); *G01N 33/24* (2013.01); *B09C 2101/00* (2013.01)

(58) Field of Classification Search
CPC ... E02D 3/126; E02D 3/12; E02D 2200/1671; E02D 5/66; E02D 7/22; B09C 2101/00; B09C 1/002; B09C 1/08

USPC ...... 405/128.5, 241, 263; 175/323, 324, 394
See application file for complete search history.

(56) References Cited

U.S. PATENT DOCUMENTS

| | | | | |
|---|---|---|---|---|
| 3,243,962 | A * | 4/1966 | Ratliff .................... | C09K 17/06 111/7.4 |
| 3,802,208 | A * | 4/1974 | Granholm ................ | E02D 3/12 175/324 |
| 4,659,259 | A * | 4/1987 | Reed ........................ | E02D 3/12 405/263 |
| 4,958,962 | A * | 9/1990 | Schellhorn ............... | E02D 3/12 405/263 |
| 5,133,625 | A * | 7/1992 | Albergo .................... | B09C 1/10 111/118 |
| 5,814,147 | A * | 9/1998 | Tallard .................... | E02D 3/12 106/900 |
| 5,904,447 | A * | 5/1999 | Sutton ...................... | B09C 1/00 175/323 |
| 6,902,352 | B2 * | 6/2005 | Kim ....................... | E02D 3/126 405/266 |

(Continued)

*Primary Examiner* — Carib A Oquendo
(74) *Attorney, Agent, or Firm* — Fresh IP PLC; Aubrey Y Chen (57) ABSTRACT

A method and a device for treating soil, by injecting a treatment product, wherein a soil auger (51) with a helical drilling blade (512) in which an outlet opening (515) is provided is driven into the soil (7), while a treatment product is injected into the soil (7), the injection pressure (P) and the injection flow rate (Q) are measured, and the injection pressure (P) is adapted as a function of a soil parameter ($K_{s,rel}$) derived from the measurement values of the injection pressure (P) and the injection flow rate (Q). The device comprises a drilling rig (5), an injecting device (2a), (2b), (2c), a measurement device (3) and a computer (4).

28 Claims, 3 Drawing Sheets

(56) References Cited

U.S. PATENT DOCUMENTS

2011/0110727 A1\* 5/2011 Plahert ..................... E02D 3/12
　　　　　　　　　　　　　　　　　　　　　405/269
2014/0231322 A1\* 8/2014 Bastiaens ................. B09C 1/00
　　　　　　　　　　　　　　　　　　　　　210/143

\* cited by examiner

METHOD AND DEVICE FOR TREATING SOIL

The present application claims priority from Belgian Patent Application No. BE-2018/5199 filed on Mar. 23, 2018, which is incorporated herein by reference.

FIELD OF THE DISCLOSURE

The present disclosure concerns, on the one hand, a method for treating soil, wherein a soil auger which comprises an outlet opening is driven into the soil and wherein a treatment product is injected into the soil via the outlet opening at different depths.

On the other hand, the present disclosure also concerns a device for treating soil, comprising a drilling rig provided with a soil auger which comprises a supply duct and at least one outlet opening connected to the supply duct, wherein the drilling rig is provided for driving the soil auger into soil, an injecting device which is provided for injecting a treatment product into the soil via the supply duct and the outlet opening, and a measurement device which is provided for measuring at least the injection pressure and the injection flow rate during the injection of the treatment product into the soil.

BACKGROUND

In this patent application, the term 'soil layer' is used in the sense of a quantity of soil material located below the ground surface which can be distinguished from adjacent soil material by its specific composition or texture, such as a clay layer or a sand layer, for example, which consist mainly of clay or sand, respectively. The term soil layer therefore also refers to a specific soil type. A soil layer or soil of course also comprises the soil water which is present therein. Treatment of soil therefore also comprises treatment of the groundwater present in the soil.

U.S. Pat. No. 4,659,259 describes a method for stabilizing an unstable clay layer, using a soil auger having a helical drilling blade in which outlet openings are provided. A treatment product which chemically reacts with clay is injected into the clay layer via the outlet openings and is mixed with the clay through the rotation of the helical blade. As a result of the chemical reaction, the clay layer is locally stabilized. The treatment product is ideally injected over the entire depth of the unstable clay layer.

A method having the features of the first paragraph of this description is also used in the remediation of polluted soil. A liquid or gaseous treatment product containing chemical products or bacteria or activated carbon, etc. which can render the pollutants in the soil or groundwater harmless is injected into the soil. Taking into account the results of prior soil investigations and potentially various parameters, including the identified concentrations of polluting parameter(s), the possible presence of degradation or daughter product(s), the geochemical state of the soil layers, the distance from the source of the pollution, the time that has passed since the moment at which pollution took place, the nature and the depth of the different soil layers in the subsoil and the direction of the groundwater flow, it is determined where and in which soil layer or soil layers the treatment product must be injected in order to render as many of the pollutants as possible harmless. In places relatively close to the source of pollution, it may thus be most efficient to inject a treatment product into the soil layer which has the smallest hydraulic conductivity at that location in comparison with the other soil layers, such as for example a clay layer. In places further away from the source of the pollution, it may then be more efficient to inject the treatment products into the soil layer which has the largest hydraulic conductivity in comparison with the other soil layers, such as for example a sand layer. When polluting products move in a certain direction underground with the groundwater flow, a treatment product can be injected into well-defined soil layers which lie on the trajectory of the groundwater flow before the pollutants have moved there, in order to form a barrier that may prevent the further movement thereof.

A method for treating polluted soil is described in US 2014/0231322 A1. This method has the properties indicated in the first paragraph of this description and provides for the use of a rod-shaped injection element with a conical head and smooth outer walls. The injection element comprises a measuring instrument in cooperation with a sensor for collecting data on the pollutants present in the soil or the soil water at various depths, and an injection part for injecting a treatment product in order to render the detected pollutants harmless. Based on the data on the pollution collected via the sensor, a control unit determines the dose of the treatment product at the various depths. The injection pressure is also controlled as a function of the data on the pollution.

As already stated above, it is of great importance in a number of soil treatments that the treatment product is predominantly injected into one or more well-defined soil layers and the injection in some treatments must also be as homogeneous as possible over the entire depth trajectory or as far as possible over the entire depth of said well-defined soil layer. In this case, it is also very important that the correct quantity of treatment product (the quantity required to achieve an effective treatment) can reach the respective soil layers with a high level of certainty.

The method known from US 2014/0231322 A1 moreover has yet another drawback. As the rod-shaped injection element is pushed or hammered into the soil, the soil around it is compacted and smeared. These phenomena of 'compaction' and 'smearing' considerably reduce the permeability of the soil at the location of the outlet openings of the injection element and make injection more difficult, as a result of which higher injection pressures need to be used to achieve a workable injection flow rate. A possible consequence of these higher injection pressures is that the injected treatment product causes undesired hydraulic fracturing of the soil, as a result of which the injected treatment product is distributed into the soil via a number of preferred paths, which is of course detrimental to the efficiency of the treatment, and even ends up at the surface via such preferred paths. Pushing or hammering the rod-shaped injection element into the ground is moreover also associated with lateral vibrations, thus forming a channel around the injection element and the extending rods above it. The injected treatment product can relatively easily be pushed upwards along the injection element via this channel (referred to below using the technical term 'blow-out').

As the injection element is pushed or hammered into the soil and as it is not possible to simultaneously push and inject, the treatment product cannot be injected into the soil at every desired depth (i.e. over the entire desired depth trajectory), and this is done, for example, only at certain discrete depths with a vertical intermediate distance of approximately 30 cm.

As a result of one or more of the drawbacks mentioned, the injected product thus very often does not reach the different soil layers intended, or only in a much smaller quantity than required. As a result, the treatment is much less efficient than expected or the processes intended with the injected product do not take place at all.

Often, investigations are carried out in advance into the distribution of the pollution in the soil by means of soil augering with associated soil sampling and analyses, monitoring wells and associated groundwater sampling and analyses and MIP/Enissa MIP probing. This allows the spread of the pollution in the soil to be mapped. These techniques can also be used to acquire an idea of the geology but only limited information is provided as to the hydraulic permeability and the injectability of the different soil layers. Another instrument used for this is known under the commercial name 'hydraulic profiling tool' or 'HPT'. A rod-shaped element with a conical point and a smooth outer side is pushed or hammered into the soil. Via a number of outlet openings in the rod-shaped element, water is injected into the soil at a low and known flow rate. Based on measurements of the injection pressure, the hydraulic conductivity can be assessed at different depths. Such preliminary soil investigation is cumbersome and time-consuming and, due to the limited volume of water injected, it can often be difficult to extrapolate the results obtained to injectability of the soil layers concerned. Moreover, the measurement values often give a distorted picture of the actual soil properties. During the insertion of the rod-shaped element into the soil, the soil is compacted by the conical point, and the soil pores are smeared closed by the smooth outer sides of the rod-shaped element. This 'compaction' and 'smearing' reduce the permeability of the soil at the location where the water is injected. As a result, the hydraulic conductivity is often underestimated, especially when injecting into heavier soil types, such as clay, loam, sandy loam and loamy sand.

SUMMARY

An object of embodiments of the present invention is to provide a method for treating soil having the features indicated in the first paragraph of this description, which is used to remedy the drawbacks indicated above, and which in particular makes it possible to inject the required quantity of treatment product into one or more well-defined soil layers in a simple, efficient and quick way and with a higher level of certainty than with the existing methods.

This object may be achieved by providing a method having the features indicated in the first paragraph of this description wherein use is made of a soil auger which comprises a helical drilling blade, wherein the outlet opening is provided in the drilling blade, wherein the injection pressure and the injection flow rate are measured during the injection, and wherein the injection pressure is adapted as a function of a soil parameter, derivable from the injection flow rate and the injection pressure, of the soil layer into which the treatment product is injected.

A soil auger with helical drilling blade can be gradually driven into the ground at a relatively slow and uniform speed by rotation around its longitudinal axis. As a result, the treatment product can be injected into the soil at any desired depth.

The soil auger may in this case be self-tapping or not, with the downwards movement requiring a downwards force on the soil auger or not. In this case, the helical blade cuts through the soil, as a result of which the soil surrounding the outer diameter of the soil auger is disturbed only very little and is barely compacted or smeared, if at all.

The structure of the different soil layers therefore remains virtually intact at the location of the outer diameter of the soil auger. As the outlet opening is provided on the outer periphery of the helical blade, the treatment product is mainly injected into this undisturbed soil. As a result, the measurements of injection pressure and injection flow rate permit a good estimation of the actual soil properties. This also allows a fairly accurate assessment of the injectability of the treatment product to be used for the soil treatment into the specific soil layer.

A significant advantage of the helical form of the soil auger is also that the soil above and below the helical blades and above the soil auger is indeed compacted, which offers the unique benefit that the injected liquid does not have the tendency at all to rise to the surface along the rods of the soil auger.

The properties of soil vary as a function of the depth. By adapting the injection pressure as a function of the properties of the soil at the depth where the treatment product is injected, it is possible to ensure that this injection pressure is kept low enough to avoid phenomena which lead to undesired movements of the treatment product in the soil, including undesired hydraulic fracturing. Partly because the rotary drilling causes hardly any lateral vibrations, virtually no channel is formed around the soil auger. This prevents the injected treatment product from easily being able to move upwards in the soil in a channel thus formed (blow-out). It is thus possible avoid the situation where the treatment product does not reach the desired soil layer or soil layers or does not reach the desired soil layer or soil layers in the foreseen and required quantity.

The adaptation of the injection pressure can be carried out manually but may also occur automatically through a regulating device provided for this purpose.

Said soil parameter is preferably the hydraulic permeability or the injectability of the fluid used (liquid, emulsion, solution, slurry or gas) or a value or a variable or a parameter which is proportionate to, or is a measure of, the hydraulic permeability of this soil or the injectability of the fluid used into this soil. It is also possible to determine two or more different soil parameters, and the injection pressure can be adapted depending on two or more different soil parameters.

The hydraulic permeability and/or said injectability are preferably derived from the ratio of the measured injection flow rate to the measured injection pressure.

During the treatment of the soil, the depth at which injection is carried out is preferably also monitored. This can be done at intervals but the depth is preferably continuously monitored for at least a part of the drilling trajectory. The injecting itself is preferably also carried out continuously for at least a part of the drilling trajectory.

Preferably, information is also provided on the injected volumes of treatment product, and on the depth and the injection pressure and the injection flow rate of the performed injections continuously or at intervals during the treatment.

During the method according to some embodiments of the invention, at least one soil layer is preferably also identified or located using said soil parameter.

In this patent application, 'identifying a soil layer' is intended to mean either that the soil type of the soil layer in question is determined or that measurement data which characterize said soil type, or values, variables or parameters derived therefrom, are noted, stored or visualized, or that corresponding signals are generated which make it possible to determine the soil type. The expression 'that the soil layer is located' is intended to mean that the depth—both the upper and lower boundary—at which a specific soil layer lies in the subsoil is determined.

The term 'depth' here is intended to refer to the distance, along the drilling trajectory, from the soil surface at the place where the soil auger is driven into the soil. During this method, the depth at which the outlet opening is located during the injection of the treatment product is preferably also noted or stored or visualized or a corresponding measurement signal is generated which is provided by a data processing unit for processing.

Preferably, during the method according to some embodiments of the invention, at least one soil layer is identified using a soil parameter which is derived from the measurement values of the injection pressure and the injection flow rate.

As a result, the identification of one or more soil layers can take place during the treatment of the soil, and using the device which is provided for the soil treatment. By also recording, in addition to the measurement values of the injection pressure and the injection flow rate, the depth at which the injection that provided these measurement values took place, the soil layer concerned can also be located. It is thus possible to ensure that the soil layer situated at this depth is the soil type into which a planned quantity of treatment product needs to be injected in order to carry out the soil treatment in an effective way. It is of course possible to locate several soil layers in this way during the treatment.

As the injection takes place in virtually undisturbed soil and due to the fact that the soil auger does not disturb the soil at the location of the injection opening, the measurements provide a realistic picture of the actual soil properties in the undisturbed state and permit effective identification of the specific soil layer.

This information on the soil properties and the composition of the soil to be derived therefrom and the precise depth of one or more soil layers at the location of the soil treatment may be very useful. This information may, for example, lead to an adjustment of the soil treatment in progress or may be used to plan future soil treatments in this location.

Preferably, all soil layers into which the soil auger penetrates during the method or all soil layers into which the fluid is injected are identified in this way.

The method in which a specific soil layer is identified and/or located may, for example, comprise the following steps, not necessarily in the order stated: at a first depth, a quantity of treatment product is injected into the soil while the injection pressure and the injection flow rate are measured; at a second depth, a quantity of treatment product is injected into the soil while the injection pressure and the injection flow rate are measured; on the basis of the measurements at the first depth it is determined that the outlet opening is in a soil layer other than the desired soil layer at the first depth; and on the basis of the measurements at the second depth it is determined that the outlet opening is in the desired soil layer at the second depth.

The identification of one or more soil layers is carried out, for example, by deriving a soil parameter from the measurement values of the injection pressure and the injection flow rate which is recognizable as typical of the soil layer. The soil parameter may represent a soil property of the soil layer or may be a parameter which is representative (is a measure) of a soil property. The soil parameter may be expressed as an absolute value or as a relative value and/or may be visualized in any way, for example in a graphic representation and/or by means of one or more values or indicators, for example on a screen.

In the method according to some embodiments of the invention, the measurement values of the injection pressure and the injection flow rate and the magnitude of the soil parameter derived therefrom do not necessarily need to be expressed numerically or graphically represented or shown by an indicator or on a screen. The injection pressure and the injection flow rate may also be measured using a measurement device which cooperates with a data processing unit which is provided in order to determine, on the basis of measurement signals or measurement data which are representative of the injection pressure and the injection flow rate, whether or not a performed injection of the treatment product was carried out in a specific soil layer, and/or to determine a soil parameter or several soil parameters. The determination that an injection was carried out in a specific soil layer and/or the (or each) soil parameter can then be communicated to an operator, for example on a screen, and/or can be converted into automatic control of an injecting device for starting the soil treatment by injecting a quantity of treatment product desired for the soil treatment into the specific soil layer via the outlet opening. In this case, the injection pressure may also be automatically adapted to the identified soil layer and/or to the soil parameter(s). Preferably, the data processing unit forms part of a computer or a PLC unit.

The product which is used to determine when the outlet opening is in a specific soil layer or to identify or locate a soil layer when it is injected by measuring pressure and flow rate may optionally differ from the product which is used to treat the soil (treatment product).

The flow rate and the pressure when injecting treatment product to treat the soil (this is referred to below using the term 'treatment injection') may differ from the injection pressure and the injection flow rate which are used when injecting treatment product, water or any other liquid to determine, by measuring pressure and flow rate, when the outlet opening is in a specific soil layer or to identify or locate a soil layer (this is referred to below using the term 'measurement injection'). The volume of product which is injected may also be different in this case.

Thus, in the measurement injection, for example, 20 litres of treatment product are injected per metre of drilling trajectory at a flow rate of 5 litres/minute. The volume and the pressure and the flow rate during a treatment injection are of course determined as a function of the pollution and, inter alia, also as a function of information on the soil type into which the injection is made and information on the injectability of the treatment product into said soil type. A typical volume, flow rate and pressure when injecting a carbon source (such as molasses, 3DMe, etc.) into a clayey soil which is polluted with chlorinated solvents is, for example, 100 litres/metre, 2 bar and 10 litres/minute. By using a soil auger with a helical drilling blade, the treatment injection can also be made into soil which is not very disturbed (not compacted), as a result of which the injection pressures used do not need to be excessively high and there is a higher level of certainty that the treatment product is distributed homogeneously through the soil layer concerned and reaches the intended depth or the intended soil layer.

The data processing unit is preferably also provided for identifying at least one soil layer other than the specific soil layer on the basis of a measurement of the injection pressure and the injection flow rate during the injection of treatment product into said other soil layer, and for communicating this identification to the operator.

When performing the method according to some embodiments of the present invention, the injection pressure is preferably adapted in such a way that it does not exceed a certain maximum value.

The hydraulic permeability of soil and the injectability of a certain fluid into soil varies as a function of the depth, mainly because the soil has a different composition and/or texture (e.g. sand, loam or clay) and/or structure at different depths. As stated, it is usually possible to distinguish different soil layers in the subsoil. A soil layer which, for example, consists mainly of sand (or generally a soil layer with good permeability) has a high hydraulic permeability or good injectability. In such a soil layer, a liquid or liquefied treatment product can already move upwards via the drill hole (blow-out) at an injection pressure of 2 bar, which is obviously undesirable.

Said maximum value is preferably determined in advance for one or more soil types or soil layers and/or depending on one or more soil parameters, such as the hydraulic permeability of the soil or the injectability of a specific fluid into the soil, in order as far as possible to prevent any undesired movement of the treatment product in this soil. However, said maximum value is usually only established or measured empirically during the injection itself.

The injection pressure is then preferably adapted in such a way during the treatment that the predetermined or empirically established maximum value of the injection pressure, associated with the identified soil type into which the injection is made and/or depending on the soil parameter(s), derived from said measurement values, of the soil into which the injection is made, is not exceeded.

Preferably, the injection pressure is adapted in order to obtain an injection flow rate which is above a specific lower limit.

At an injection pressure of 1 bar in a soil layer with good permeability (consisting, for example, mainly of sand), an acceptable injection flow rate of 12 litres per minute is already obtained.

In a soil layer with poor permeability which, for example, mainly consists of clay and thus has a much lower hydraulic permeability (or injectability), an injection pressure of 1 bar, for example, will result in an injection flow rate of only approximately 0.5 litre per minute. At such an injection flow rate, the treatment will take so much time that the method is no longer sufficiently viable from an economic perspective. In this clay soil with poor permeability, it is often possible to inject at a much higher pressure, for example 5 to 7 bar, in which case an economically viable injection flow rate (e.g. 10 litres/min.) is indeed achieved without any risk of blow-out, hydraulic fracturing or daylighting (the undesired appearance of the treatment product in a random place at the surface).

When adapting the injection pressure in a method according to some embodiments of the present invention, the injection pressure is preferably adapted such that the injection flow rate remains sufficiently high, with a view to ensuring that the required quantities of treatment product reach the respective soil layers while achieving an economically viable speed at which the treatment is performed.

Said lower limit is, for example, 5 litres per minute or 8 litres per minute or 10 litres per minute.

In a particularly preferred method according to an embodiment of the present invention, the treatment product is continuously injected into the soil for at least a part of the movement trajectory of the soil auger in the soil, while the injection pressure and the injection flow rate are measured and while the injection pressure is continuously adapted as a function of said soil parameter of the soil into which the treatment product is injected.

As a result, it is possible to determine how one or more soil properties vary within a certain depth range in the subsoil and, if necessary, to adapt the injection pressure in order to optimize the treatment as explained above. Due to these continuous measurements, the presence of soil layers which extend over only a small depth can be reliably identified and treated if necessary.

Said soil parameter is preferably the hydraulic conductivity, or a measure of the hydraulic conductivity of the soil at the location where the treatment product is injected.

This property identifies the most common soil types and accordingly provides information on the spreading behaviour of the soil pollution and the injectability of the soil layer concerned. Using this property, one soil type can be distinguished from other soil types and the different soil layers can thus be identified. By way of example, a number of common soil types are listed below in order of increasing hydraulic conductivity: heavy clay, clay, loam, sandy loam, light sandy loam, loamy sand and sand.

According to a preferred method, the treatment product is continuously or at intervals injected into the soil for at least a part of the movement trajectory of the soil auger, while the injection pressure and the injection flow rate are measured, and the soil layer present at a number of different depths is identified or located on the basis of the measurements.

According to a specific method, for at least one soil layer, the depths at which the top and bottom of the soil layer are located are determined on the basis of the measurements.

This information is particularly useful when the soil treatment requires the treatment product to be injected as far as possible over the entire depth of a specific soil layer. Preferably, for each soil layer which the soil auger penetrates on its movement trajectory, the depths at which the top and bottom of the soil layer are located are determined.

The treatment product is preferably a product with a soil-remediating, a soil-stabilizing or soil-fixing effect. It comprises, for example, chemicals and/or bacteria and/or a carbon source and/or activated carbon or a combination/mixture of the above and is selected as a function of its properties in order to dissolve and/or degrade the pollutants present in the soil and/or covert them into less harmful substances or render them less harmful in any way or via any process. These treatment products are known to the person skilled in the art who is active in this sector. They include oxidants, reductants, acids, bases, carbon sources, nutrients, (emulsified) oils, salts and organic compounds. Specific examples are potassium sulfate, lactate, persulfate, activated persulfate, sodium hydroxide, molasses, emulsified vegetable oil, or liquid activated carbon (this list is non-exhaustive). Combinations of two or more different active substances in the same treatment product are also possible, for example to deal with contamination involving two or more pollutants or to treat contamination involving one pollutant via various processes or reactions at the same time.

The method according to some embodiments of the invention may be used, for example, for treating soil which has been contaminated with chlorinated aliphatic hydrocarbons such as, for example, tetrachloroethene, through the homogeneous injection of a suitable carbon source. Through the stimulating effect on the existing microbial activity in the soil, this carbon source leads to strongly reducing anaerobic conditions in which the polluting tetrachloroethene is gradually dechlorinated by the bacteria present in the soil and is converted into trichloroethene and then into dichloroethene and vinyl chloride and eventually into harmless ethene.

Soils which, for example, are contaminated with the following substances may also be treated using methods according to embodiments of the present invention: mineral oil components, petroleum hydrocarbons, methyl tert-butyl ether, benzene, toluene, ethylbenzene, xylene, chlorinated aliphatic hydrocarbons, polyaromatic hydrocarbons, polychlorinated biphenyls (PCBs), heavy metals, acids and bases, PFOS, PFAS and PFOA (this list is also non-exhaustive).

The treatment product is preferably in liquid or gaseous form. The term 'in liquid form' here does not only cover a liquid but also other injectable forms, including a mixture, a solution, a suspension, an emulsion, a sol, a slurry, a colloidal mixture or a gel. Combinations of two or more forms in the same product are also possible.

Preferably, the magnitude of the injection pressure and the injection flow rate, and/or the magnitude of said soil parameter derived from the injection pressure and the injection flow rate are noted and/or stored and/or visualized for a number of different depths, for at least a part of the downwards movement trajectory of the soil auger.

Preferably, the magnitude of the injection pressure and the injection flow rate, or the magnitude of a soil parameter derived from the injection pressure and the injection flow rate is noted and/or stored and/or visualized together with the associated depth for at least a part of the downwards movement trajectory. As a result, the findings made during the soil treatment may be clearly observed by an operator and the method can also be quickly adjusted if necessary.

The information relating to the injection pressure and/or the injection flow rate and/or the soil parameter derived therefrom may also, for example, only be used to control a drilling and injecting device in order to at least partially automate the method.

The information relating to the injection pressure and/or the injection flow rate and/or the soil parameter derived therefrom may also, for example, only be used to unambiguously report the injection process, wherein the distribution of the injected product over the injected soil trajectory and/or the applied injection pressures as a function of the depth and/or the injection flow rates as a function of the depth and/or the permeability and/or injectability of the injected soil trajectory are shown/reported either in numerical form or as a graphic representation.

In a most preferred method, the helical drilling blade is provided on the outside of a drilling core which comprises a supply duct for the product, the helical drilling blade comprises at least one injection zone in which the drilling blade is formed by two walls which are at a distance from one another along the longitudinal direction of the drilling core and are separated by an intermediate space, and said outlet opening is formed between the outer edges of these walls. Such a soil auger can be of relatively simple design and can spread the treatment product within a large range surrounding the soil auger. Due to the fact that the treatment product flows out laterally from the outer side of the helical blade, the treatment product also enters barely disturbed soil. This ensures an ideal homogeneous penetration into and thus treatment of the soil.

The part of the helical drilling blade where the drilling blade is formed by two walls which are at a distance from one another along the longitudinal direction of the drilling core and are separated by an intermediate space is called the injection zone. The helical drilling blade is, for example, of a double-walled configuration over this part of its length, when viewed along the helical course. The outer edges of the walls which form the helical drilling blade are the edges which are furthest from the axis of the drilling core. These walls themselves are preferably also helical. The two walls have, for example, the same wall thickness while the intermediate distance between the two walls, for example, is virtually identical to the wall thickness. The outlet opening is preferably connected to the supply duct provided in the drilling core via the intermediate space between the two walls. Due to the double-walled configuration of the helical drilling blade, the soil at the location of the point where the product is inserted into the soil is barely compacted or smeared, if at all. As a result, it is routinely possible to work with a lower injection pressure yet still generate an acceptable (economically viable) and workable injection flow rate. This lower pressure means that there is also a much lower risk of the product not reaching the correct location in the subsoil due to phenomena such as daylighting, blow-out and undesired fracturing (undesired blasting of the soil as a result of which the product ends up in an undesired place in the soil).

A method for treating soil, in which a soil auger with a helical drilling blade according to the paragraph above is used, may also be performed without the use of the characterizing features of the soil auger comprising a helical drilling blade, the outlet opening being provided in the drilling blade, measuring the injection pressure (P) and the injection flow rate (Q) during the injection, and the injection pressure (P) being adapted as a function of a soil parameter, derivable from the injection flow rate (Q) and the injection pressure (P), of the soil into which the treatment product is injected. In other words, a method having exclusively the following features also expressly falls under the methods presented in this description:

a method for treating soil by injecting a treatment product into a specific soil layer of the soil, wherein a soil auger which comprises a helical drilling blade and which comprises an outlet opening is driven into the soil until the outlet opening is in the soil, and wherein the treatment product is injected into the soil via the outlet opening, characterized in that the helical drilling blade is provided on the outside of a drilling core which comprises a supply duct for the product, in that the helical drilling blade comprises at least one injection zone in which the drilling blade is formed by two walls which are at a distance from one another along the longitudinal direction of the drilling core and are separated by an intermediate space, and in that said outlet opening is formed between the outer edges of these walls.

The additional features of the method mentioned below which relate to the soil auger are not only integrable into the described method, but are also integrable into the method which was described in the preceding paragraph of this description.

Said injection zone describes, for example, an injection angle of at least approximately 180° or at least approximately 360° about the axis of the drilling core. In a number of different embodiments, this injection angle is, for example, at least 15° or at least 30° or at least 45° or at least 60° or at least 90° or at least 120°. As a result, the treatment product is distributed through a considerable proportion of the soil located around the soil auger. At an injection angle of at least approximately 360° or, in other words, an injection angle which corresponds to at least approximately one full turn or rotation of the helical drilling blade around the drilling core, the treatment product is injected into the soil located around the soil auger in all directions.

The range of the treatment product is thus ideal, meaning that a particularly efficient soil treatment is achieved.

In a furthermore specific method according to some embodiments of the invention, a soil auger is used in which the drilling core has a tip end and a rear end and in which the drilling blade has a front end facing the tip end, the drilling blade comprises a first zone, where the outer diameter of the drilling blade, from the front end, increases from a first diameter to a second diameter, the drilling blade comprises a second zone adjoining the first zone, where the outer diameter is the second diameter, and the injection zone of the drilling blade is situated substantially within the second zone.

The drilling blade preferably has a third zone adjoining the second zone, where the outer diameter of the drilling blade increases in the direction of the rear end from the second diameter to a third diameter. As a result, the passage which the soil auger formed in the soil is closed off above the place where the injection takes place. The soil is also compacted there to a certain degree. As a result, it will be very difficult for the treatment product to be able to move upwards. This is not connected with any drawbacks for the injection itself and the associated measurements since the injection occurs from the injection zone which is located lower down.

The drilling blade may be configured in such a way that, in the injection zone, it has a thickness which is greater than the maximum thickness of the drilling blade in the first zone. In this way, no cavity is created in the soil when the ground is situated at the level of the injection zone. This reduces the chance of injection liquid being injected into another soil layer via these cavities.

The drilling blade is further preferably configured in such a way that, in the third zone, it has at least virtually the same thickness as in the second zone. In this way, no cavity is created in the soil when the ground is situated at the level of this third zone. This reduces the chance of injection liquid being injected into another soil layer via these cavities or of the injection liquid finding a preferred path to the surface along the smooth extension rods via these cavities.

The outlet opening is preferably slit-shaped. In this case, the length of the outlet opening—measured along the helical course of the drilling blade—is greater than the height of the outlet opening—measured along the longitudinal direction of the drilling core—wherein the ratio between the length and the height of the outlet opening is preferably at least 2 or at least 3 or at least 5 or at least 10 or at least 15.

The above-mentioned object of embodiments of the present invention may also be achieved by providing a device having the features indicated in the second paragraph of this description wherein, according to the some embodiments of the present invention, the soil auger comprises a helical drilling blade in which said outlet opening is provided, and wherein the device comprises a data processing unit which cooperates with the measurement device and is provided for adapting the injection pressure (P) depending on measurement data generated by the measurement device or measurement signals relating to the injection pressure and the injection flow rate which were used during the injection of a quantity of treatment product.

The advantages of using a soil auger having a helical drilling blade in which the outlet opening is provided have already been indicated above. Once again, the main advantages are that the treatment product can be injected into virtually undisturbed soil and that this can consequently be carried out at an injection flow rate which is low enough to ensure a homogeneous distribution of the treatment product in a specific soil layer, and that driving a soil auger into the ground without hammering causes virtually no lateral vibrations, as a result of which there is also no passage channel formed around the soil auger along which the treatment product can move upwards.

Preferably, the data processing unit is provided for deriving a soil parameter of the soil on the basis of measurement data generated by the measurement device or measurement signals relating to the injection pressure and the injection flow rate which were used during the injection of a quantity of treatment product, and for adapting the injection pressure as a function of said soil parameter.

Said soil parameter is, for example, the hydraulic conductivity, or a measure of the hydraulic conductivity, of the type of soil of which the soil layer is composed. It may also be (a measure of) the injectability of the fluid used into the soil in which the injection took place. It is also possible to derive two or more soil parameters from the measurement data or measurement signals, and the injection pressure can be adapted depending on two or more soil parameters.

The data processing unit is, for example, a computer or a PLC unit.

Identifying or locating a specific soil layer in the subsoil is also carried out using the same device as the device with which the soil treatment is carried out and may also form part of the method for treating the soil. Since the injection moreover also takes place in virtually undisturbed soil as a result of using said soil auger, the measurements provide a more realistic picture of the actual soil properties in the undisturbed state and, for example, they allow a soil layer to be identified or located in a particularly effective way.

The data processing unit is preferably provided for identifying or locating at least one soil layer on the basis of the measurement data or measurement signals.

The device for treating soil according to some embodiments of the present invention is preferably provided for continuously injecting the treatment product into the soil for at least a part of the movement trajectory of the soil auger in the soil, while the injection pressure and the injection flow rate are measured and while the injection pressure is continuously adapted as a function of said soil parameter of the soil into which the treatment product is injected.

Said soil parameter is preferably the hydraulic conductivity or a measure of the hydraulic conductivity, of the soil at the location where the treatment product is injected.

In a highly preferred embodiment, the device is provided for injecting the treatment product into the soil continuously or at intervals for at least a part of the movement trajectory of the soil auger in the soil, while the injection pressure and the injection flow rate are measured, and the device is provided for adapting the injection pressure and/or identifying or locating at least one soil layer on the basis of the measurement data or measurement signals.

Preferably, the magnitude of the injection pressure and the injection flow rate, or the magnitude of a soil parameter derived from the injection pressure and the injection flow rate is in this case noted and/or stored and/or visualized together with the associated depth for at least a part of the downwards movement trajectory of the soil auger. As a result, the findings made during the soil treatment may be clearly observed by an operator, the method can also be quickly adjusted if necessary, and the saved or stored information may also subsequently be used as evidence that the performed injection was correctly performed or may also be utilized for planning later soil treatments.

In a particularly preferred device, the device comprises a soil auger which comprises an elongate drilling core, the drilling core comprises a supply duct for the treatment product, the helical drilling blade comprises at least one injection zone in which the drilling blade is formed by two walls which are at a distance from one another along the longitudinal direction of the drilling core and are separated by an intermediate space, and said outlet opening is formed between the outer edges of these walls.

The helical drilling blade, in other words, is of a double-walled configuration over a part of its length, when viewed along the helical course, and this part of the helical drilling blade is referred to by the term injection zone. The outer edges of the walls which form the helical drilling blade are the edges which are furthest from the axis of the drilling core. These walls themselves are preferably also helical. The two walls have, for example, the same wall thickness while the intermediate distance between the two walls is virtually identical to the wall thickness. The outlet opening is preferably connected to the supply duct via the intermediate space between the two walls.

A device for treating soil, in which a soil auger with a helical drilling blade according to the paragraph above is used, may also be configured without the use of in the third zone, the drilling blade having at least virtually the same thickness as in the second zone. In other words, a device having exclusively the following features also expressly falls under the devices presented in this description:

Device for treating soil, comprising a drilling rig provided with a soil auger which comprises a supply duct and at least one outlet opening connected to the supply duct, wherein the drilling rig is provided for driving the soil auger into soil, an injecting device which is provided for injecting a treatment product into the soil via the supply duct and the outlet opening, and a measurement device which is provided for measuring at least the injection pressure and the injection flow rate during the injection of the treatment product into the soil, characterized in that the soil auger comprises an elongate drilling core, in that the drilling core comprises a supply duct for the treatment product, in that the helical drilling blade comprises at least one injection zone (IZ) in which the drilling blade is formed by two walls which are at a distance from one another along the longitudinal direction of the drilling core and are separated by an intermediate space, and in that said outlet opening is formed between the outer edges of these walls.

The additional features of the device mentioned below which relate to the soil auger are not only integrable into the device described previosuly, but are also integrable into the method which was described in the preceding paragraph of this description.

Said injection zone describes, for example, an injection angle of at least approximately 180° or at least approximately 360° about the axis of the drilling core. In a number of different embodiments, this injection angle is, for example, at least 15° or at least 30° or at least 45° or at least 60° or at least 90° or at least 120°. As a result, the treatment product is distributed within a considerable range in the soil located around the soil auger. At an injection angle of at least approximately 360° or, in other words, an injection angle which corresponds to at least approximately one full turn or rotation of the helical drilling blade around the drilling core, the treatment product is injected into the soil located around the soil auger in all directions. The distribution of the treatment product is thus ideal, meaning that a particularly efficient soil treatment is achieved.

The device may be configured in such a way that the drilling core has a tip end and a rear end, that the drilling blade has a front end facing the tip end, that the drilling blade has a first zone, where the outer diameter of the drilling blade, from the front end, increases from a first diameter to a second diameter, and that the drilling blade comprises a second zone adjoining the first zone, where the outer diameter is the second diameter, and that the injection zone of the drilling blade is situated substantially within the second zone.

The drilling blade preferably comprises a third zone adjoining the second zone, where the outer diameter of the drilling blade increases in the direction of the rear end from the second diameter to a third diameter. As a result, the passage which the soil auger formed in the soil is closed off above the place where the injection takes place. The soil is also compacted there to a certain degree. As a result, it will be very difficult for the treatment product to be able to move upwards. This is not connected with any drawbacks for the injection itself and the associated measurements since the injection occurs from the injection zone which is located lower down.

The drilling blade may be configured in such a way that, in the injection zone, it has a thickness which is greater than the maximum thickness of the drilling blade in the first zone. In this way, no cavity is created in the soil when the ground is situated at the level of the injection zone. This reduces the chance of injection liquid being injected into another soil layer via these cavities.

The drilling blade is further preferably configured in such a way that, in the third zone, it has at least virtually the same thickness as in the second zone. In this way, no cavity is created in the soil when the ground is situated at the level of this third zone. This reduces the chance of injection liquid being injected into another soil layer via these cavities.

The outlet opening is preferably slit-shaped. In this case, the length of the outlet opening—measured along the helical course of the drilling blade—is greater than the height of the outlet opening—measured along the longitudinal direction of the drilling core—wherein the ratio between the length and the height of the outlet opening is preferably at least 2 or at least 3 or at least 5 or at least 10 or at least 15.

The drilling core may be provided at the rear end with connecting means for coupling the soil auger to a tube element which extends the soil auger. The tube element preferably has an internal duct which adjoins the supply duct when the soil auger and the tube element are coupled to one another. The tube element preferably also has connecting means which are complementary to the connecting means of the drilling core, so that the coupling can be realized through the cooperation of these connecting means.

BRIEF DESCRIPTION OF THE DRAWINGS

In order to illustrate the invention and to indicate further features and advantages thereof, a more detailed description of a preferred embodiment of a device for remediating soil according to the present invention will now be given. This description will also explain in further detail the features of the method according to the present invention.

It will be clear that this preferred embodiment of the device is only one of the many embodiments which are possible within the scope of protection of the patent which is defined by the attached claims, and that nothing in the following description can be seen as a limitation of this scope.

Reference numerals are used in this description to refer to the attached drawings, in which.

DETAILED DESCRIPTION OF EMBODIMENTS

Figure 1:
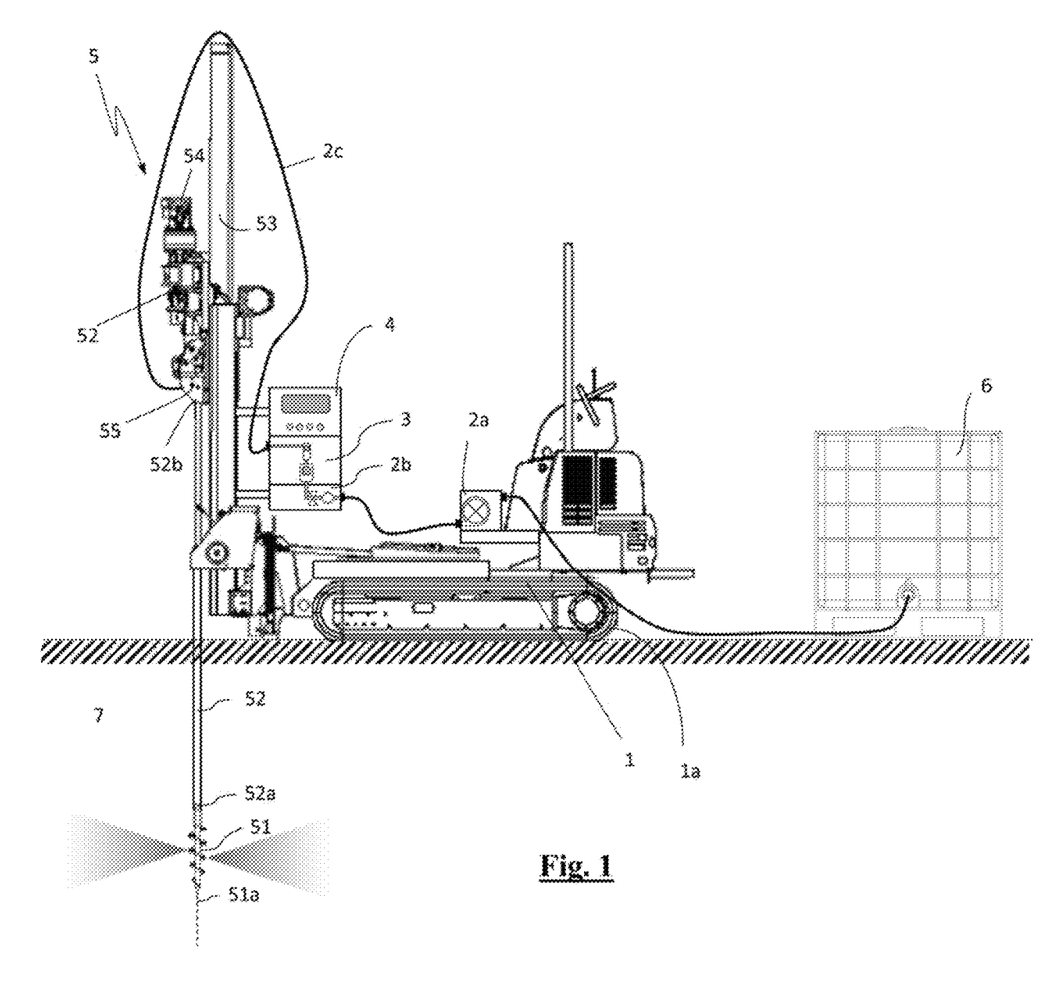
FIG. 1 is a side view of the device for remediating soil according to the present invention, wherein the soil auger is situated in soil which is shown in cross section.

The device shown in FIG. 1 comprises a mobile chassis (1) which is movable on caterpillar tracks (1a) and a reservoir (6) which is arranged in a fixed position on the surface of soil (7) and which contains a supply of a liquid chemical product. The product is suitable for degrading a pollutant present in the soil (7) and converting it into harmless substances.

The mobile chassis (1) carries an injecting device consisting of a pump system (2a), a regulating device (2b) and a flexible supply pipe (2c). Furthermore, the chassis (1) also carries a measurement device (3), a computer (4) and a drilling rig (5).

The drilling rig (5) comprises a self-tapping soil auger (51) which is held in a chuck (52) and drive means (54) in order to transfer a torque to the soil auger (51) in order to rotate it about its longitudinal axis (51a). The chuck is detained in a vertically positioned guide structure (53) so as to be movable in a vertical direction.

Figure 2:
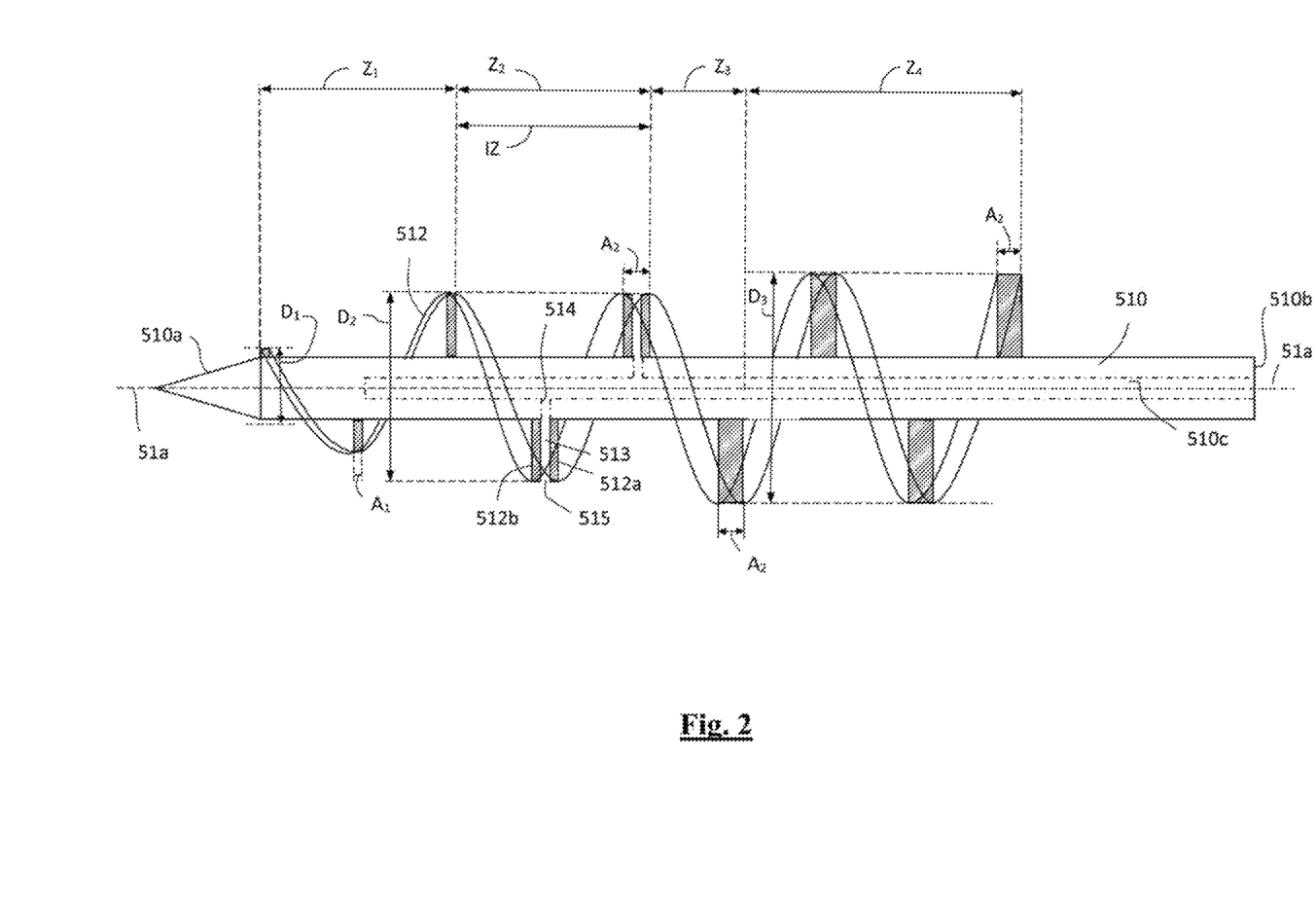
FIG. 2 shows a part of the soil auger illustrated in FIG. 1, wherein the drilling blade is diagrammatically shown by indication of the helical upper surface and the helical lower surface of the drilling blade and local cross sections of the drilling blade situated in a vertical plane of symmetry.

As can most clearly be seen in FIG. 2, the soil auger (51) consists of a hollow, tubular drilling core (510), in which a cylindrical supply duct (510c) extending along the longitudinal axis (51a) is provided, and the outside of which is provided with a helical drilling blade (512). The supply duct (510c) opens out into the rear end (510b) of the drilling core (510). The drilling core (510) has a pointed tip end (510a) and is provided with connecting means (not shown in the drawings) at the rear end (510b) in order to connect the soil auger (51) to a tube element (52)—see FIG. 1—in which a central duct (not shown in the drawings) is provided that opens out at both ends (52a), (52b) of the tube element (52). The tube element (52) is provided at one end (52a) with connecting means (not shown in the drawings) which are complementary to the connecting means which are provided at the rear end (510b) of the drilling core (510). In the connected position, the soil auger (51) and the tube element (52) extend in line with one another (as shown in FIG. 1), while the supply duct (510c) of the drilling core (51) adjoins the central duct of the tube element (52).

At the top end (52b), the tube element (52) is connected to the drive means (54) of the drilling rig (5) so that a torque can be transferred to the tube element in order to rotate the entirety of the tube element (52) and the soil auger (51) connected thereto. As a result of this rotation, the pointed tip end (510a) of the soil auger (51) will penetrate further into the soil (7) through the action of the helical drilling blade (512).

The central duct of the tube element (52) is also connected, at the top end, to the flexible supply pipe (2c) of the injecting device. This connection occurs via a known coupling element (55) which is suitable for connecting a rotating duct—the central duct of the tube element (52)—to a non-rotating duct—the supply pipe (2c).

The injecting device is provided for pumping the product out of the reservoir (6) by means of the pump system (2a) and for moving it under pressure via the regulating device (2b), the flexible supply pipe (2c), the coupling element (55), the central duct of the tube element (52) and the supply duct (510c) of the soil auger (51) and finally injecting it into the soil (7) via an outlet opening (515), provided in the drilling blade (512), which is connected to the supply duct.

The helical drilling blade (512) of the soil auger (51) has an injection zone (IZ) which extends over a full turn of the drilling blade (512), and with the drilling blade (512) being formed from two helical walls (512a), (512b) which are a distance apart from one another along the longitudinal direction (51a) of the drilling core (510) and are separated by an intermediate space (513) which is connected to the supply duct (510c) via an opening (514) in the wall of the drilling core (510), and thus forms an outlet opening (515) for the product.

The outlet opening (515) is consequently a slit-shaped opening which follows the helical course of the drilling blade (512) over a full turn. As a result, this outlet opening (515) is situated at the outer edge of the drilling blade (512), and thus makes it possible to inject the liquid product sideways into the soil (7) from the outermost edge of the drilling blade (512).

The drilling blade (512) has a first zone ($Z_1$), where the outer diameter of the drilling blade (512), from the front end, increases from a first diameter ($D_1$) to a second diameter ($D_2$), and a second zone ($Z_2$) adjoining the first zone ($Z_1$), where the outer diameter maintains the second diameter ($D_2$). The injection zone (IZ) with the slit-shaped outlet opening (515) is situated substantially within the second zone ($Z_2$). In the injection zone (IZ), the drilling blade (512) has a thickness ($A_2$) which is greater than the maximum thickness ($A_1$) of the drilling blade in the first zone ($Z_1$).

The drilling blade (512) has a third zone ($Z_3$) adjoining the second zone ($Z_2$) where the outer diameter of the drilling blade increases in the direction of the rear end (512b) from the second diameter ($D_2$) to a third diameter ($D_3$) and a fourth zone ($Z_4$) adjoining the third zone ($Z_3$) where the outer diameter of the drilling blade is the third diameter ($D_3$).

In the third zone ($Z_3$) and in the fourth zone ($Z_4$), the drilling blade (512) has virtually the same thickness ($A_2$) as in the second zone ($Z_2$).

The wall thickness (A1) of the drilling blade in the first zone is, for example, 4 mm. In the injection zone (IZ), the two walls (512a), (512b) have the same wall thickness of, for example, 4 mm, while the distance between the two walls, and thus also the height of the outlet opening (515), is also 4 mm. The total thickness of the drilling blade in the injection zone is therefore 12 mm. The wall thickness of the drilling blade in the third and the fourth zone is, for example, likewise 12 mm.

The diameter of the drilling core (510) is, for example, 30 mm. In the first zone (Z1), the drilling blade has a width, which gradually increases from 2 mm to 30 mm. As the drilling core has a diameter of 30 mm, this means that the first diameter (D1) of the drilling blade is 32 mm and gradually increases to a second diameter (D2) which is 60 mm. Said third diameter (D3) is then, for example, 70 mm. The distance between two successive turns of the helical drilling blade is, for example, 90 mm.

The liquid product is injected into the soil for the entire trajectory covered by the soil auger (51) in the soil, until the outlet opening (515) is situated at a depth of approximately 7.5 m. The regulating device regulates the pressure (P) at which the product is injected.

The measurement device (3) also continuously measures the depth of the outlet opening, the total injected volume (V), the injection pressure (P) and the injection flow rate (Q), and these measurement data (respectively expressed in cm with respect to the soil surface, litres, litres per hour and bar) are sent to the computer (4) where a soil parameter ($K_{s,rel}$) is calculated on the basis of the measurement results, said parameter being a relative measure for the hydraulic conductivity of the soil (7) at the different depths. The measured values of volume, pressure and flow rate and the associated soil parameter ($K_{s,rel}$) and the associated depths are stored in the memory of the computer and also represented numerically and/or graphically on the computer screen (4a) as a function of the depth. Such a possible graphic representation is shown in FIG. 3.

In the graphic representation of the soil parameter ($K_{s,rel}$), it is readily possible to distinguish the zones (8) with a relatively high hydraulic conductivity and the zones (9) with a relatively low hydraulic conductivity.

Based on this numerical and/or graphic information, it can be established with a high level of certainty during the soil treatment when the outlet opening (515) of the soil auger (51) is situated at a specific depth or in that specific soil layer into which the product must be injected in order to render the pollutant harmless in the most efficient way.

Figure 3:
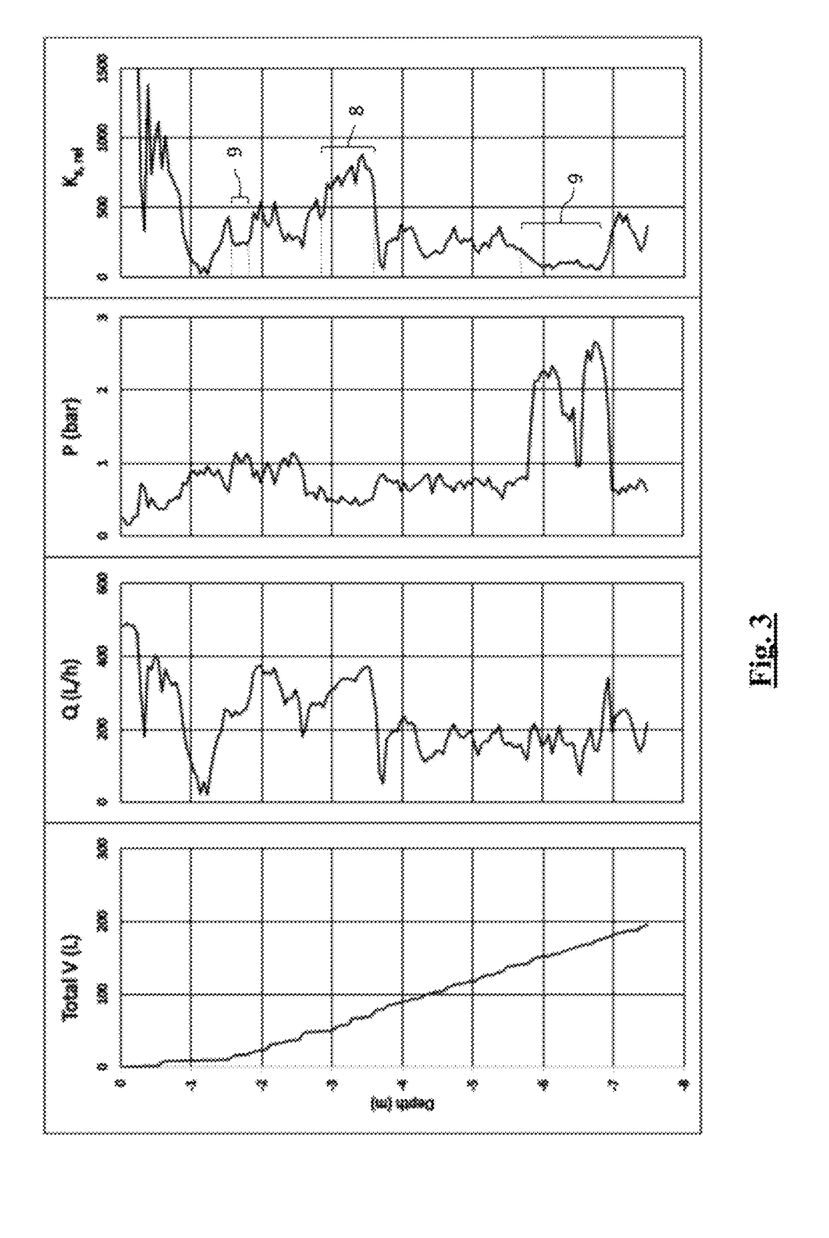
FIG. 3 shows the graphic representations of the measurement data which are recorded during the movement trajectory of the soil auger from the soil surface to a depth of approximately 7.5 metres.

From the information shown in FIG. 3, it is possible to infer, for example, that there is a very thin soil layer with poor permeability (e.g. a clay layer) between 1.6 and 1.8 m deep, that there is a soil layer with good permeability (e.g. a sand layer) between 2.9 m and 3.6 m deep, and that there is once again a soil layer with poor permeability between 5.7 m and 6.8 m deep.

It should thus be possible to degrade or treat pollutants, which are known to accumulate mainly in soil layers with poor permeability, in a very efficient way by injecting the product into the soil (7) for the entire trajectory of the soil auger (51) and, on the basis of the information shown in FIG. 3, doing the following:

- when the outlet opening (515) is at a depth between 1.6 m and 1.8 m, determining on the basis of the values of the soil parameter ($K_{s,rel}$) that the outlet opening is situated in a thin soil layer with poor permeability at these depths (the soil layer may, for example, be identified as a clay layer),
- injecting the necessary volume of product into the first clay layer at an adapted pressure in order to degrade the pollutants present therein,
- when the outlet opening (515) is at a depth between 2.9 m and 3.6 m, determining on the basis of the values of the soil parameter ($K_{s,rel}$) that the outlet opening (515) is situated in a thicker soil layer with poor permeability at these depths (this soil layer may also be identified as a clay layer), and
- injecting the necessary volume of product into the second clay layer at an adapted pressure in order to degrade the pollutants present therein.

Such a method and device is simpler and more effective than the known methods. As emphasized above, the area of application is not limited to the remediation of soil alone, but such a method and such a device may also be used in any possible form of soil treatment wherein a liquid or gaseous product is injected into soil and where it may be appropriate to inject the product into one or more well-defined soil layers or soil types. Another area of application, for example, is injecting soil-compacting, soil-fixing or soil-stabilizing substances into soil.

As the measurement device (3) continuously measures, visualizes (in numerical form) and also continuously records the time, the depth, the injection pressure and the injection flow rate, it is possible to be aware at any moment during the soil treatment of the depth at which injection is taking place, the volumes of treatment product which have already been injected and must still be injected (as compared to the volume requested/stipulated by the client), the injection pressure and injection flow rate at which injection is currently being carried out, and the permeability of the subsoil at that depth (to be inferred from the injection flow rate/injection pressure ratio).

Meanwhile, the injection pressure can be manually adjusted at any time. During the injection process, the injection pressure must, on the one hand, be kept as high as possible in order to achieve a sufficiently large injection flow rate (otherwise the injection takes too much time and is no longer viable from an economic perspective), but, on the other hand, this injection pressure should also not be too high in order to prevent the phenomena referred to above (daylighting, blow-out, undesired fracturing).

A potential additional advantage of the method and the device according to some embodiments of the present invention is that, based on data continuously recorded during the treatment relating to time, depth, injection pressure and injection flow rate, a graphic representation can be created of the injected volumes, of the injection pressure and of the injection flow rate as a function of the depth. This graphic representation shows whether or not the product can be inserted in the desired location and in the desired quantity. This graphic representation may also indicate the depths at which problems have occurred, how these were solved, and why the desired quantity of treatment product, for example, has not reached the soil layer for which it was intended.

Using the continuously recorded injection flow rate/injection pressure ratio, it is also possible to generate a cross section of the subsoil, on which the relative permeability of the soil trajectory is visualized. On this cross section, it is then possible to identify the presence of soil layers with good, less good and poor permeability. This information may be useful in providing additional information as to the spread of the initial soil contamination, on the one hand, and as to the possible spread of the injected product with and into the groundwater, on the other.

The invention claimed is:

1. Method for treating soil, comprising:
   driving a soil auger, which comprises an outlet opening, into the soil;
   injecting a treatment product into the soil via the outlet opening at different depths;
      wherein the soil auger comprises a helical drilling blade and the outlet opening is provided in the drilling blade;
   measuring an injection pressure and an injection flow rate during the injection;
   deriving a soil parameter from the injection flow rate and the injection pressure of the soil at the location where the treatment product is injected; and
   adapting the injection pressure as a function of the soil parameter, said soil parameter being a hydraulic conductivity, a measure of the hydraulic conductivity, or a value, a variable, or a parameter which is proportionate to the hydraulic conductivity.

2. Method for treating soil, according to claim 1, further comprising identifying or locating at least one soil layer using said soil parameter.

3. Method for treating soil, according to claim 1, characterized in that the injection pressure is adapted in order to obtain an injection flow rate which is above a certain lower limit.

4. Method for treating soil, according to claim 1, characterized in that the injection pressure is adapted in such a way that it does not exceed a certain maximum value.

5. Method for treating soil, according to claim 1, characterized in that the treatment product is continuously injected into the soil for at least a part of a movement trajectory of the soil auger in the soil, while the injection pressure and the injection flow rate are measured and while the injection pressure is continuously adapted as a function of said soil parameter of the soil into which the treatment product is injected.

6. Method according to claim 1, characterized in that the treatment product is continuously or at intervals injected into the soil for at least a part of a movement trajectory of the soil auger, while the injection pressure and the injection flow rate are measured, and further comprising identifying or locating a soil layer present at a number of different depths on the basis of the measurements.

7. Method according to claim 6, further comprising, for at least one soil layer, determining depths at which a top and a bottom of the soil layer are located on the basis of the measurements.

8. Method according to claim 1, characterized in that the product is a product with a soil-remediating or soil-stabilizing effect.

9. Method according to claim 1, further comprising noting and/or storing and/or visualizing the magnitude of the injection pressure and the injection flow rate, and/or the magnitude of said soil parameter derived from the injection pressure and the injection flow rate for a number of different depths, for at least a part of a movement trajectory of the soil auger.

10. Method according to claim 1, characterized in that the helical drilling blade is provided on the outside of a drilling core which comprises a supply duct for the product, the helical drilling blade comprises at least one injection zone in which the drilling blade is formed by two walls which are at a distance from one another along a longitudinal direction of the drilling core and are separated by an intermediate space, and said outlet opening is formed between outer edges of the two walls.

11. Method for injecting a product into soil, according to claim 10, characterized in that said injection zone describes an injection angle of at least 15° or at least 180° or at least 360° about an axis of the drilling core.

12. Method for injecting a product into soil, according to claim 10, characterized in that the drilling core has a tip end and a rear end, the drilling blade has a front end facing the tip end, and the drilling blade has a first zone, where the outer diameter of the drilling blade, from the front end, increases from a first diameter to a second diameter, and the drilling blade comprises a second zone adjoining the first zone, where the outer diameter is the second diameter, and the injection zone of the drilling blade is situated within the second zone.

13. Method for injecting a product into soil, according to claim 12, characterized in that the drilling blade comprises a third zone adjoining the second zone, where the outer diameter of the drilling blade increases in the direction of the rear end from the second diameter to a third diameter.

14. Method for injecting a product into soil, according to claim 12, characterized in that, in the injection zone, the drilling blade has a thickness which is greater than a maximum thickness of the drilling blade in the first zone.

15. Method for injecting a product into soil, according to claim 12, characterized in that, in the third zone, the drilling blade has at least virtually the same thickness as in the second zone.

16. Method for injecting a product into soil according to claim 10, characterized in that a width of the outlet opening measured along a helical course of the drilling blade is greater than a height of the outlet opening, wherein a ratio between the width and the height of the outlet opening is preferably at least 2 or at least 3 or at least 5 or at least 10 or at least 15.

17. Device for treating soil, comprising:
a drilling rig provided with a soil auger which comprises a supply duct and at least one outlet opening connected to the supply duct, wherein the drilling rig is provided for driving the soil auger into soil,
an injecting device which is provided for injecting a treatment product into the soil via the supply duct and the outlet opening, and
a measurement device which is provided for measuring at least injection pressure and injection flow rate during the injection of the treatment product into the soil,
wherein the soil auger comprises a helical drilling blade in which said outlet opening is provided,
wherein the device comprises a data processing unit which cooperates with the measurement device and is provided for deriving a soil parameter of the soil based on measurement data generated by the measurement device or measurement signals relating to the injection pressure and the injection flow rate which were used during the injection of a quantity of treatment product, and
wherein the device is provided for adapting the injection pressure as a function of said soil parameter, said soil parameter being a hydraulic conductivity, a measure of the hydraulic conductivity, or a value, a variable, or a parameter which is proportionate to the hydraulic conductivity.

18. Device for treating soil according to claim 17, characterized in that the data processing unit is provided for identifying or locating at least one soil layer on the basis of the measurement data or measurement signals.

19. Device for treating soil according to claim 17, characterized in that the device is provided for continuously injecting the treatment product into the soil for at least a part of a movement trajectory of the soil auger in the soil, while the injection pressure and the injection flow rate are measured and while the injection pressure is continuously adapted as a function of said soil parameter of the soil into which the treatment product is injected.

20. Device for treating soil according to claim 17, characterized in that the device is provided for injecting the treatment product into the soil continuously or at intervals for at least a part of a movement trajectory of the soil auger in the soil, while the injection pressure and the injection flow rate are measured, and the device is provided for adapting the injection pressure and/or identifying or locating at least one soil layer on the basis of the measurement data or measurement signals.

21. Device for treating soil, according to claim 17, characterized in that the soil auger comprises an elongate drilling core, the drilling core comprises a supply duct for the treatment product, the helical drilling blade comprises at least one injection zone in which the drilling blade is formed by two walls which are at a distance from one another along a longitudinal direction of the drilling core and are separated by an intermediate space, and said outlet opening is formed between the outer edges of the two walls.

22. Device for treating soil, according to claim 21, characterized in that said injection zone describes an injection angle of at least 180° or at least 360° about an axis of the drilling core.

23. Device for treating soil, according to claim 21, characterized in that the drilling core has a tip end and a rear end, the drilling blade has a front end facing the tip end, and the drilling blade has a first zone, where the outer diameter of the drilling blade, from the front end, increases from a first diameter ($D_1$) to a second diameter ($D_2$), and the drilling blade comprises a second zone ($Z_2$) adjoining the first zone ($Z_1$), where the outer diameter is the second diameter ($D_2$), and the injection zone (IZ) of the drilling blade is situated substantially within the second zone ($Z_2$).

24. Device for treating soil, according to claim 23, characterized in that the drilling blade comprises a third zone adjoining the second zone, where the outer diameter of the drilling blade) increases in the direction of the rear end from the second diameter to a third diameter.

25. Device for treating soil, according to claim 23, characterized in that, in the injection zone, the drilling blade has a thickness which is greater than a maximum thickness of the drilling blade in the first zone.

26. Device for treating soil, according to claim 21, characterized in that, in the third zone, the drilling blade has at least virtually the same thickness as in the second zone.

27. Device for treating soil according to claim 17, characterized in that a width of the outlet opening measured along a helical course of the drilling blade is greater than a height of the outlet opening, wherein a ratio between the width and the height of the outlet opening is preferably at least 2 or at least 3 or at least 5 or at least 10 or at least 15.

28. Device for treating soil according to claim 17, characterized in that the drilling core comprises a connector at the rear end for connecting the drilling core to a tube element which extends the soil auger.

* * * * *